(12) United States Patent
Liu et al.

(10) Patent No.: US 8,895,775 B2
(45) Date of Patent: Nov. 25, 2014

(54) METHOD FOR PREPARING CONJUGATED DIENE PHOSPHONATE COMPOUNDS

(75) Inventors: Zhaoqing Liu, Shanghai (CN); Floryan De Campo, Shanghai (CN)

(73) Assignee: Rhodia Operations, Aubervilliers (FR)

( * ) Notice: Subject to any disclaimer, the term of this patent is extended or adjusted under 35 U.S.C. 154(b) by 34 days.

(21) Appl. No.: 13/502,791

(22) PCT Filed: Oct. 30, 2009

(86) PCT No.: PCT/CN2009/074726
§ 371 (c)(1),
(2), (4) Date: Apr. 19, 2012

(87) PCT Pub. No.: WO2011/050533
PCT Pub. Date: May 5, 2011

(65) Prior Publication Data
US 2012/0202957 A1 Aug. 9, 2012

(51) Int. Cl.
 C07F 9/40 (2006.01)
 C08F 30/00 (2006.01)
 C07F 9/02 (2006.01)
 C07F 9/38 (2006.01)
(52) U.S. Cl.
 CPC .................................. C07F 9/3826 (2013.01)
 USPC .................... 562/8; 526/278; 568/14; 562/19
(58) Field of Classification Search
 USPC .................... 526/275, 278; 562/19, 8; 568/14
 See application file for complete search history.

(56) References Cited

U.S. PATENT DOCUMENTS

| | | |
|---|---|---|
| 4,170,609 A | 10/1979 | Turner |
| 4,201,669 A | 5/1980 | Becker |
| 4,446,046 A | 5/1984 | Becker |
| 4,507,249 A | 3/1985 | Pieper et al. |
| 4,526,788 A | 7/1985 | Murdock et al. |
| 4,605,779 A | 8/1986 | Matsuda et al. |
| 5,391,816 A | 2/1995 | Tomko |
| 5,811,575 A | 9/1998 | Kleiner et al. |
| 6,497,687 B1 | 12/2002 | Blanco |
| 7,442,831 B2 * | 10/2008 | Dabdoub .......................... 562/8 |

OTHER PUBLICATIONS

Arbuzov, B.A. Bulletin of the Academy of Sciences of the USSR, Division of Chemical Science, 24 (6), 1975, p. 1285-1289.*
Rowe, B.J. Tetrahedron: Asymmetry 12 (2001) p. 1701-1708.*

* cited by examiner

*Primary Examiner* — Jafar Parsa
*Assistant Examiner* — Amy C Bonaparte

(57) ABSTRACT

It is provided a method for preparing conjugated diene phosphonate compounds with high reactivity, which can be used to prepare a variety of phosphonate-bearing conjugated dienes. Some of those dienes will become reactive monomers to make polymers and co-polymers. The said method comprises the step of reacting α, β- or β, γ-unsaturated ketones or aldehydes with phosphorus acid or its derivates optionally in a mixture of acetic anhydride and/or acetic acid, to obtain a conjugated diene phosphonate compound having the formula (III)

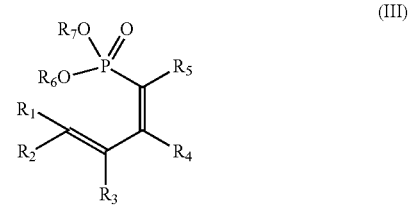

(III)

18 Claims, No Drawings

METHOD FOR PREPARING CONJUGATED DIENE PHOSPHONATE COMPOUNDS

CROSS REFERENCE TO RELATED APPLICATIONS

This application claims priority to international application no. PCT/CN2009/074726, filed Oct. 30, 2009. The contents of the aforementioned application are incorporated herein in their entirety.

TECHNICAL FIELD

This invention relates to a method for preparing conjugated diene phosphonate compounds, especially relates to a method for preparing phosphonated monomer with higher reactivity.

BACKGROUND

Vinyl monomers containing phosphonic acid groups have various applications in industry, for example, their polymer and co-polymers are used as corrosion inhibitor in cooling or boiler water system (U.S. Pat. Nos. 4,446,046 and 4,201,669); as dispersants in water treatment and pigment dispersion. Various type of vinyl monomers were described in prior arts, such as 1-phenylvinyl phosphonic acid (U.S. Pat. No. 5,391,816), vinyl phosphonic acid (U.S. Pat. Nos. 6,479,687, 5,811,575), acrylamidomethylpropanephosphonic acid (U.S. Pat. No. 4,526,788), isopropenyl phosphonic acid (U.S. Pat. No. 4,446,046), chloride substituted phenylvinyl phosphonic acid (U.S. Pat. No. 4,507,249) and diene type of phosphonic acid monomer (U.S. Pat. No. 4,507,249). However, some of those monomers were prepared from very hazardous raw materials of phosphorus chlorides, $PCl_3$ or/and phosphorus acid ($H_3PO_3$), or phosphorus hexoxide, ($P_4O_6$), or from complicated and expensive processes or/and have limited reactivity toward polymerization.

Recent U.S. Pat. Nos. 7,420,081 and 7,442,831 patents described a new way to prepare some of the above monomers from ketone or aldehyde with phosphorus acid in a mixture of acetic acid and acetic anhydride. These monomers include alkyl and aryl substituted vinyl phosphonic acids of lower reactivity toward polymerization. It is still desirable to have an economic process to produce more reactive phosphonic acid-containing monomers.

In the literature the reactivity of $\alpha,\beta$-unsaturated carbonyl compounds has been widely studied and Mauser (Chem. Rev., 1963, 63 (3), pp 311-324) specifically studied the reactivity of mesityl oxide. Typically such compounds can either react at the carbonyl or at the C=C double bond. Usually, the reaction at the carbonyl with strong nucleophilic compounds such as Grignard reagents afford the corresponding hydroxyl adducts or the allenes (1,2-dienes) if the dehydration takes place. When the reactions take place at the double bond with other nucleophilic compounds such as amines or alcohols the mechanism is a 1,4 addition leading to the formation of the corresponding ketone. In particular the reaction of mesityl oxide with dialkylphosphites leads selectively to the formation of the ketones.

SUMMARY OF THE INVENTION

In general, this invention relates to a method for preparing conjugated diene phosphonate compounds with high reactivity, which comprises the step of reacting $\alpha,\beta$- or $\beta,\gamma$-unsaturated ketones or aldehydes having the formula I or II, with phosphorus acid or its derivatives optionally in a mixture of acetic anhydride and/or acetic acid.

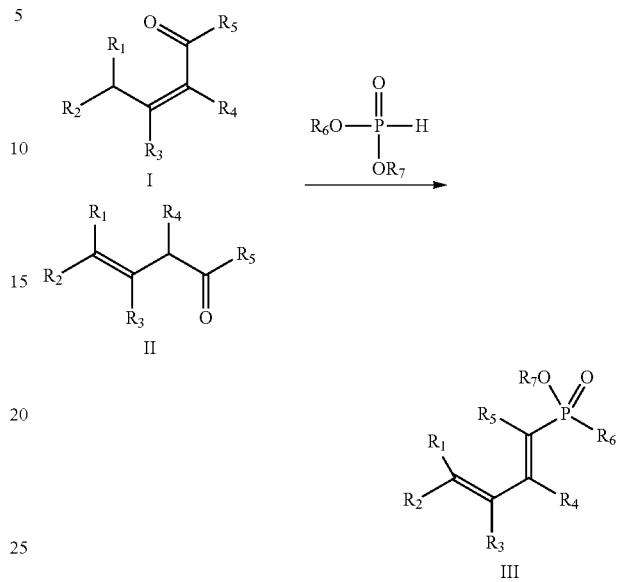

The method of the present invention can be used to prepare a variety of phosphonate-bearing conjugated dienes. Some of those dienes will become reactive monomers to make performance polymers and co-polymers. These polymers could find applications in water treatment, oilfield applications, surface treatment applications, mining, dental application, plastics, etc.

Also, the monomers prepared according to the present invention alone could be used for the previous applications and provide the advantage that they could be polymerized at surfaces much easier than current commercial monomers.

DETAILED DESCRIPTION OF THE INVENTION

In one aspect, the present invention provides a method for preparing conjugated diene phosphonate compounds from $\alpha,\beta$- or $\beta,\gamma$-unsaturated ketones or aldehydes, which comprises reacting an $\alpha,\beta$- or $\beta,\gamma$-unsaturated ketone or aldehyde having the formula I or II,

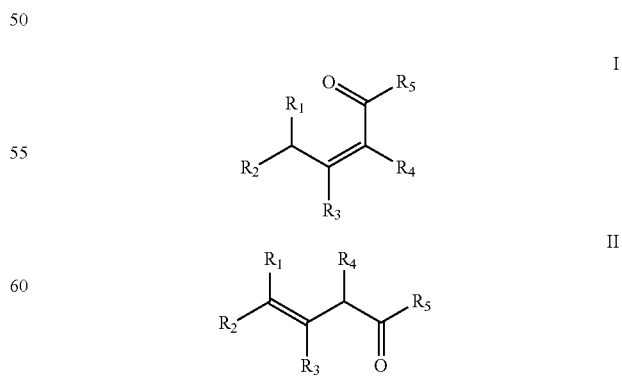

With a phosphorus acid or its derivatives having the structure,

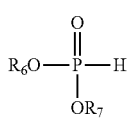

To obtain a conjugated diene phosphonate compound having the formula III,

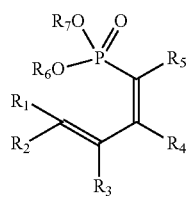

Wherein, $R_1$, $R_2$, $R_3$, $R_4$, and $R_5$ represent, independently, hydrogen, alkyl, aryl, alkaryl, aralkyl, cycloalkyl, heterocyloalkyl, or alkenyl groups; preferably, the said alkyl and alkenyl comprise from 1~24 carbon atoms, said aryl comprises from 6~24 carbon atoms, said alkaryl, aralkyl comprise from 7~24 carbon atoms, and said cycloalkyl, heterocycloalkyl comprise from 3~24 carbon atoms; more preferably, the said alkyl and alkenyl comprise from 1~18 carbon atoms, said aryl comprises from 6~18 carbon atoms, said alkaryl, aralkyl comprise from 7~18 carbon atoms, and said cycloalkyl, heterocycloalkyl comprise from 3~18 carbon atoms.

Preferably, $R_1$ and/or $R_2$ represent hydrogen, so the monomers so obtained are more reactive toward polymerization.

Preferably, $R_1$, $R_2$ and $R_4$, represent hydrogen; or preferably, $R_3$ and $R_5$ represent methyl. More preferably, $R_1$, $R_2$, and $R_4$ represent hydrogen and $R_3$, $R_5$ represent methyl.

$R_6$ and $R_7$ represent, independently, hydrogen, alkyl, aryl, alkaryl, aralkyl, cycloalkyl, alkenyl groups, or metals selected from the group consisting of Na, Li, Ca. Preferably, the said alkyl and alkenyl comprise from 1~24 carbon atoms, said aryl comprises from 6~24 carbon atoms, said alkaryl, aralkyl comprise from 7~24 carbon atoms, and said cycloalkyl, heterocycloalkyl comprise from 3~24 carbon atoms; more preferably, the said alkyl, alkenyl comprise from 1~18 carbon atoms, said aryl comprises from 6~18 carbon atoms, said alkaryl, aralkyl comprise from 7~18 carbon atoms, and said cycloalkyl, heterocycloalkyl comprise from 3~18 carbon atoms.

Preferably, $R_6$, and $R_7$ represent hydrogen.

In one of the preferred embodiments of the present invention, any two of $R_1$, $R_2$, $R_3$, $R_4$ and $R_5$ are together formed into a cycloalkyl, or heterocycloalkyl group, which is preferably selected from 5, 6, 7 and 8 membered rings.

In another one of the preferred embodiments of the present invention, $R_6$ and $R_7$ are together formed into a cycloalkyl, or heterocycloalkyl group, which is preferably selected from 5, 6, 7 and 8 membered rings.

Unless otherwise defined herein or below in the remainder of the specification, "Compounds of the present invention" or "compounds prepared according to the present invention" refers to compounds encompassed by the various description and structural formula disclosed herein. The compounds may be identified by either their chemical structure and/or chemical name.

The compounds of the present invention may contain one or more chiral centers and/or double bonds and therefore may exist as stereoisomers, such as Z- and E- or cis- and trans-isomers from cyclic structures or double bonds (i.e., geometric isomers), rotamers, enantiomers or diastereomers. Accordingly, when stereochemistry at chiral centers is not specified, the chemical structures depicted herein encompass all possible configurations at those chiral centers including the stereoisomerically pure form (e.g. geometrical isomerically pure, enantiomerically pure or diastereomerically pure) and enantiomeric and stereoisomeric mixtures, with the exception that when only one enantiomer is specified, the structure includes the other enantiomer as well. For example, in the event that a compound of formula III disclosed in the present invention is Z-form or trans-form for the double bonds close to P, one skilled in this art should understand that the E-form or cis-form of the compound is also disclosed. Enantiomeric and stereoisomeric mixtures can be resolved into their component enantiomers or stereoisomers using separation techniques or chiral synthesis techniques well known to those skilled in this art.

According to the method of the present invention, said compound I or II is added in the molar ratio of (1~1.5):1 relative to said phosphorus acid or its derivatives; or preferably (1~1.2):1 relative to said phosphorus acid or its derivatives. The reaction time remains 4~24 hours, or preferably 4-8 hours. The reaction temperature remains at 0~100° C., or preferably 20~60° C.

The reaction according to the present invention may be optionally carried out under protection of inert gas protection. Said inert gas may be selected from, for example, one or more of the group consisting of nitrogen, argon, and carbon dioxide.

One potential mechanism to explain the selectivity of the reactions would be a concerted addition-dehydration mechanism with an oxaphosphirane intermediate (P—C—O membered ring). The presence of phosphonate and allylic protons could explain the ease of dehydration steps observed experimentally to afford the conjugated double bonds.

This one-step addition and dehydration mechanism could be depicted as below. Oxaphosphirane (P—C—O membered ring) is considered as an intermediate, followed by elimination and rearrangement to form the diene. Both the phosphonate and allylic proton facilitate the formation of the conjugated C=C double bonds:

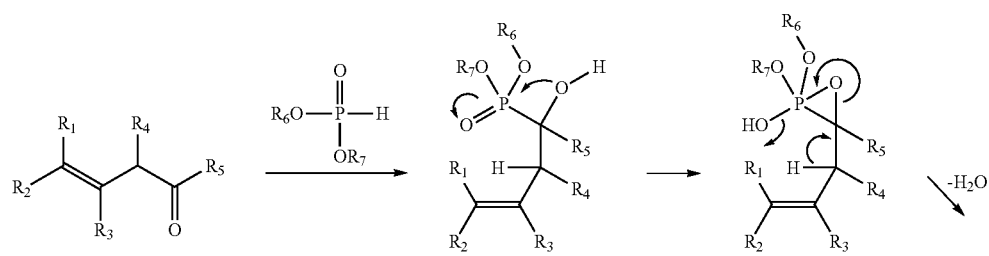

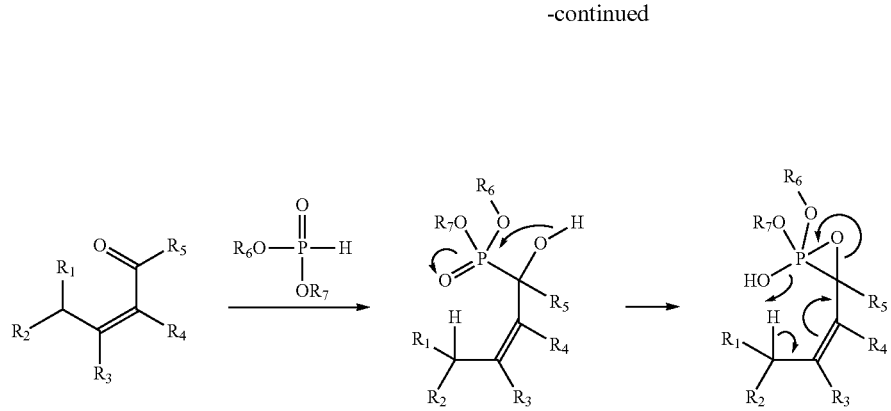

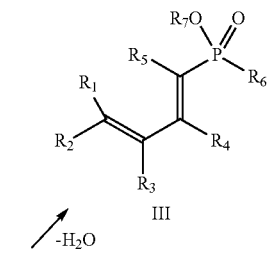

Without wishing to be bound by any existing theory, the preparation method of the present invention is valid whether starting from α,β-unsaturated carbonyl compounds or α,γ-unsaturated carbonyl compounds and both species will lead to the formation of the same diene.

For example, mesityl oxide, was reacted with phosphorus acid in the presence of acetic anhydride and acetic acid under mild conditions to yield 4-methylpenta-2,4-diene-2-phosphonic acid in more than 90% mole purity.

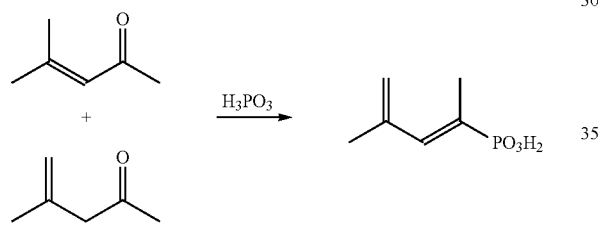

Unlike the reaction described in U.S. Pat. Nos. 7,420,081 and 7,442,831, the formation of the diene monomer involves the rearrangement of the existing double bond if α,β-unsaturated carbonyl compounds are used and the formation of the diene monomer requires much lower reaction temperature in a single step. This behavior has not been described in prior arts even if no C=C rearrangement occurs in the case of β,γ-unsaturated ketones or aldehydes.

The unsaturated ketones and aldehydes can be obtained from aldol condensations of carbonyl compounds.

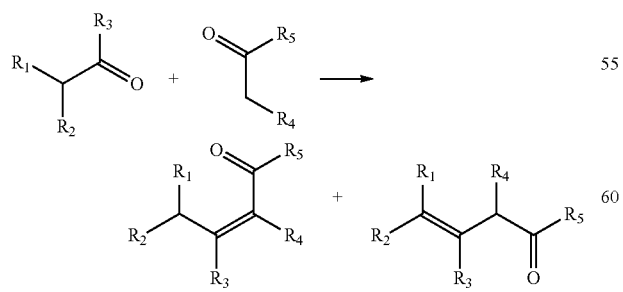

For example, dimerization of methyl isobutyl ketone (MIBK) as taught by U.S. Pat. No. 4,170,609.

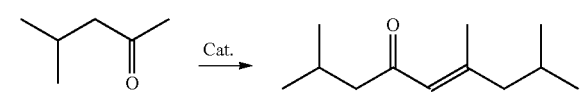

In a similar manner, aldol condensation of pinacolone will yield a highly branched unsaturated ketone:

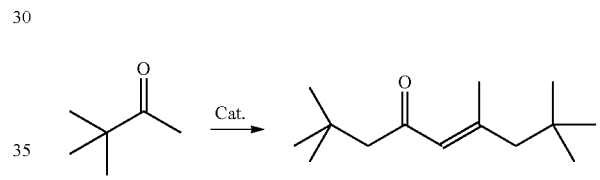

Following are some of the commercially available unsaturated ketones and aldehydes. They are important industrial chemicals. They are used as solvents, for example, mesityl oxide, as precursor to other commodity and specialty chemicals, for example, isophorone and as monomer for polymeric materials, for example, methyl vinyl ketone (MVK).

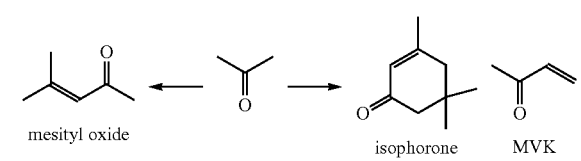

3-Methylcrotonaldehyde is a precursor for Vitamin A. Industrially, it is produced from isobutene and formaldehyde:

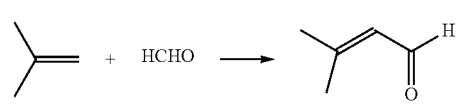

The most attractive one may be crotonaldehyde. It is a biogenic compound, used as florvoring agent. It can be produced from renewable resources of bioethanol:

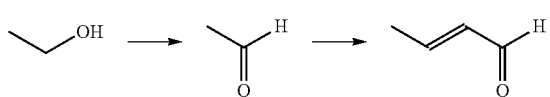

2-Ethyl acrolein, and its isomer of tiglic aldehydes are intermediate for flavor agents (U.S. Pat. No. 4,605,779):

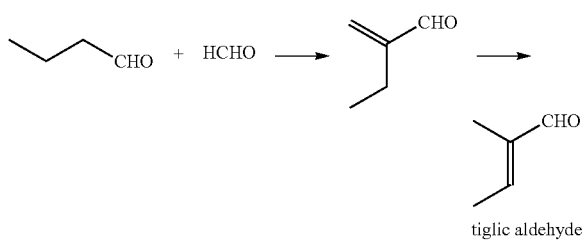

Natural unsaturated ketones and aldehydes can also be used to carry out the reaction. Those include, for example, piperitone, carvone, umbellulone, menthene-2-one, menthene-3-one, verbenone and myrtenal. The resulting phosphonate dienes could be of important biological activities, thus as insecticides, pesticides, pharmaceuticals and their intermediates.

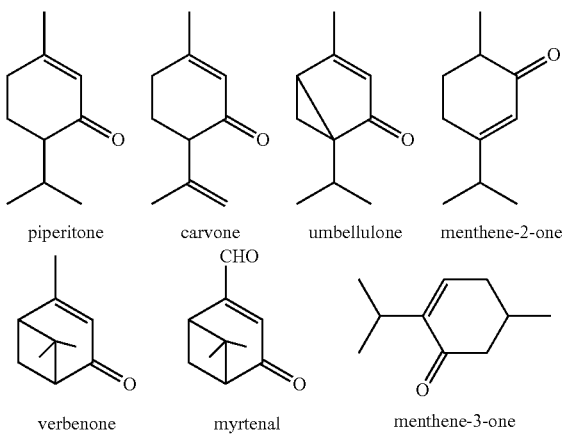

In one other aspect of the invention, the phosphonate diene prepared according to the method of the present invention can be used for making polymers or co-polymers. In this aspect the invention also relates to a polymer or co-polymer of said conjugated diene phosphonate compounds. The invention also relates to a method for preparing polymers or co-polymers of the phosphonate diene, comprising a step of preparing a phosphonate diene according to the method of the present invention and a polymerization or co-polymerization step.

In one other aspect of the present invention, the phosphonate diene prepared according to the method of the present invention, or the polymer or co-polymer can be used as flame retardants, as intermediates for active pharmaceuticals and agrochemicals, as reactive or functional monomers, typically for functional polymers, such as phosphonate-containing polystyrene, polyethylene, polypropylene, poly(meth)acrylates, poly(meth)acrylamide, polybutadiene, polyacrylonitrile, etc. and their copolymers, or building blocks for other useful products. For example, but not to limit this invention, the phosphonate diene prepared according to the method of the present invention, or the polymer or co-polymer can be used in water treatment applications, in oilfield applications, in surface treatment applications, in mining applications, in dental applications, in plastics, and etc. . . . . . Preferably, the phosphonate diene prepared according to the method of the present invention, or the polymer or co-polymer can be used as flame retardants in plastics or textile. The invention also relates to methods comprising these uses.

Flame Retardants

Phosphonate functionalities are well known to provide flame retardant (FR) properties but their synthesis is often difficult and expensive. The process according to the present invention allows a direct access to phosphonate moieties from inexpensive raw materials. The products obtained can also be further reacted to prepare some polymers. The monomers and/or the polymers should provide some significant flame retardant properties if incorporated to plastics, textiles or any other materials.

Pharma Intermediates:

The conjugated dienes prepared according to the process of the present invention may be active or intermediates for pharmaceuticals or/and agroculture chemicals.

Phosphonate compounds are well known to have unique properties and are widely used in the pharmaceutical industry. The compounds described here would provide new and unique entitis that could be used to design new drugs. These is compounds could also find some use in agriculture.

Functional Monomers:

Phosphonate monomers are scarce and typically difficult and expensive to prepare. Also, most of them have a limited reactivity which makes them difficult to use as functional monomers to combine them with other monomers (styrene, ethylene, butadiene, acrylic acid etc. . . . ). Incorporating phosphonate moieties into polymers can provide unique properties to the resulting materials such as better mechanical properties, flame retardant properties, sequestration properties, anti-bacterial properties etc. the diene monomer can also be grafted onto synthetic or natural occurring polymers.

The present invention also provides polymers prepared from conjugated diene phosphonate compounds of the formula III according to the present invention.

Phosphonating Agent:

Incorporating phosphonate groups is difficult and is typically done by using expensive reagents. The method described in the present invention could be used to functionalize various groups such as alcohols, amines, thiols or any other nucleophilic compounds by a simple Michael addition. Also, these compounds should be able to add across aromatic rings by a Friedel and Craft mechanism. Another example would to use these dienes in Diels and Alder reactions.

For example, Michael addition to give surfactants:

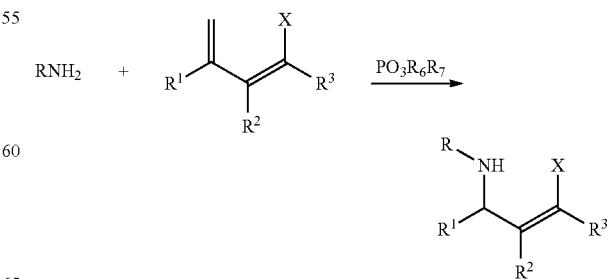

where $R_6$ or/and $R_7$ can be H.

Those from long chain aldehydes and ketones such as MIBK dimer could be used as surfmers or metal extractants Advantages of the present invention are as follows:

1) The invention provides a process to make 1,3-diene phosphonate in one step under mild conditions and using readily available and affordable raw materials. This process is a significant improvement in term of ease of process and cost.

2) The 1,3-diene phosphonate prepared according the present invention allows to develop some original polymers and composition that were not accessible before.

Very few 1,3-diene phosphonate compounds are reported in the literature and many different structures of unsaturated carbonyl compounds are readily accessible which can offer a wide range of new compounds of general formula:

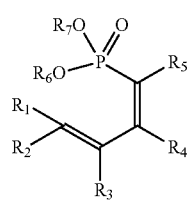

III

3) The technical solution of the present invention is kind to the environment. Using sustainable and natural raw materials is critical today and many unsaturated ketones or aldehydes are actually natural products.

The invention is further described by the examples below.

EXAMPLES OF THE PRESENT INVENTION

The following examples are offered to illustrate, but not to limit the present invention.

Example 1

Phosphorus acid, $H_3PO_3$ 200 g, which was dried for about 4 hrs at 50° C. under vacuum, and 194 g of acetic acid were added to a 2 L flask with cooling. Then 494 g of acetic anhydride was charged and the temperature rose to 25° C. to yield a colorless homogenous mixture. 1 g of phenothiazine was added and the reaction mixture became light orange. Mesityl oxide (a mixture of 1,2 and 1,3 isomers) 284 g was added drop-wise with stirring over about 4 hrs and the temperature was kept at 23~25° C. The color of the reaction mixture became dark orange after the unsaturated ketone addition. The mixture was then heated to 48° C. for 7 hrs. The reaction was monitored by $^{31}P$ NMR ($D_2O$) in term of % mole as shown in the following table:

| | Peak, δ | | | |
|---|---|---|---|---|
| Rx time, h | The unknown, 39~32 ppm | Product, 20 ppm | Anhydrides of the Product, 11 ppm | $H_3PO_3$ 4 ppm |
| 0 | 8.34 | 35.65 | 11.6 | 44.05 |
| 1 | 8.12 | 37.05 | 13.52 | 39.37 |
| 2 | 10.33 | 47.70 | 19.02 | 22.12 |
| 3 | 11.52 | 46.82 | 22.82 | 16.92 |
| 4 | 11.95 | 43.77 | 24.07 | 15.67 |
| 7 | 9.47 | 37.25 | 56.70 | 0 |

The product, 4-methyl-2,4-pentadiene-2-phosphonic acid (PoDM) and its anhydride derivative were observed in more than 90% selectivity with 100% conversion of phosphorus acid.

Example 2

620 g of the reaction mixture from Example 1 was slowly mixed with 75 ml of water. The resulting solution was heated at 50° C. for 5 hrs until no product derivative was observed as monitored by $^{31}P$ NMR in $D_2O$. After the reaction was finished, acetic acid was removed under vacuum of 5 mPa at 50° C. for 6 hrs until no solvent came out to 250 g of brown oil. $^{31}P$ NMR showed 87.4% mole is the product, while HPLC analysis showed 96.1% area at UV of 214 nm and 87.3% area at UV of 254 nm HPLC-MS analysis showed the molecular weight of the product to be 162.1 and both C-13 and H-1 NMR confirmed the structure of PoDM. The product can be further purified by extraction. Thus crude product 12.02 g was mixed with 0.52 g sodium hydroxide and 20 ml of water. The mixture was extracted with 15 ml of ethyl acetate each for 3 times. The combined organic phase was then washed with 8 ml water each for 3 times. The purity of PoDM increased from 81.2% to 94.4% by mole according to $^{31}P$ NMR analysis (20.1 ppm, $D_2O$). LC-MS showed its molecular ion at 163.1 and its dimerics at 325.1 (ES-API positive). $^1H$ and $^{13}C$ NMR (DMSO) confirmed its structure. $^1H$ NMR ($D_2O$, ppm): δ 6.30 (d, 1H), 4.95 (s, 1H), 4.79 (s, 1H), 1.78 (d, 3H) and 1.75 (s, 3H). $^{13}C$ ($D_2O$, ppm), δ 141.6 (d), 141.1 (d), 126.7 (d), 21.8 (s), 13.4 (d).

Example 3

Phosphorus acid, 10 g, dried for 4 hours at 50° C. under vacuum and 14.2 g of mesityl oxide of mixed isomers were mixed in a flask at 28° C. The mixture turned black and $^{31}P$ NMR showed 90% of phosphorous acid was reacted. Then 24.7 g of acetic anhydride was added slowly with mixing over 45 min while the temperature was kept at about 28° C. The mixture was heated to 48° C. for 4 hrs. 98% $H_3PO_3$ conversion was observed with 86% selectivity for PoDM and its anhydride derivatives.

Example 4

This reaction was similar to Example 3, except the reaction was carried out at 3~5° C. No reaction was observed before acetic anhydride addition. $^{31}P$ NMR showed 87% conversion of $H_3PO_3$ and 86% selectivity for PoDM and its anhydride derivatives.

Example 5

$H_3PO_3$ was dried for about 4 hrs at 50° C. under vacuum. 10 g of dried $H_3PO_3$ and 12.43 g of mesityl oxide were mixed in a flask at 28~30° C. Then 24.7 g of acetic anhydride was added slowly with mixing over 50 mins while the reaction temperature was kept below 30° C. The mixture was kept stirring at this temp for 4 hrs. $^{31}P$ NMR showed 81.2% conversion of $H_3PO_3$ and 86% is selectivity for PoDM and its anhydride derivatives.

Example 6

$H_3PO_3$ was dried for about 4 hrs at 50° C. under vacuum. 10 g of dried $H_3PO_3$ was dissolved in 9.7 g of acetic acid to make solution A. Then 14.2 g of mesityl oxide, 24.7 g of acetic anhydride and 0.01 g of Phenothiazine was charged in a flask and heated to 60° C. Solution A was added dropwise. The mixture was kept stirring at 60° C. for 4 hrs. $^{31}$P NMR showed 88.3% conversion of $H_3PO_3$ and 86% selectivity for PoDM and its anhydride derivatives.

Example 7

$H_3PO_3$ was dried for about 4 hrs at 50° C. under vacuum. 10 g of dried $H_3PO_3$ was dissolved in 12.35 g of acetic acid to make solution A. Then 14.2 g of mesityl oxide, 12.35 g of acetic anhydride and 0.01 g of phenothiazine was mixed together to make solution B. Next a three-necked flask was put in a oil bath at 60° C. and then Solutions A and B were added dropwise and simultaneously over 70 min After the addition, the mixture was kept stirring for another 4 hrs. $^{31}$P NMR showed 97.5% conversion of $H_3PO_3$ and 87% selectivity for PoDM and its anhydride derivatives.

Example 8

To a one-liter flask were added 100 g of phosphorus acid, 245.2 g of acetic anhydride and 97 g of acetic acid and the mixture was stirred at 14° C. Mesityl oxide, 142.2 g was drop-wise added over 2 h with mixing and batch temperature increased to 32° C. The reaction mixture was heated to 48° C. for 4 h. Then the solvent was removed at 0.1 MPa and 80° C. for 5 h. The product turned into a gel and further drying of the jelly-like product at 5 Pa and 80° C. resulted in a hard solid polymeric product, which was found not soluble in water.

What is claimed is:

1. A method for preparing conjugated diene phosphonate compounds from α,β- or β,γ-unsaturated ketones or aldehydes, which comprises, reacting an α,β- or β,γ-unsaturated ketone or aldehyde having the formula I or II,

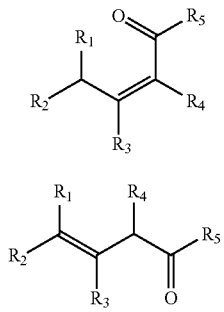

with a phosphorus acid or its derivatives having the structure,

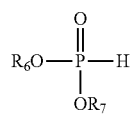

to obtain a conjugated diene phosphonate compound having the formula III,

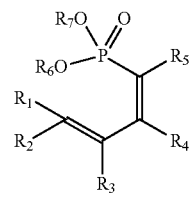

wherein,
$R_1$, $R_2$, $R_3$, $R_4$, and $R_5$ represent, independently, hydrogen, alkyl, aryl, alkaryl, aralkyl, cycloalkyl, heterocycloalkyl, or alkenyl groups;
$R_6$ and $R_7$ represent, independently, hydrogen, alkyl, aryl, alkaryl, aralkyl, cycloalkyl, alkenyl groups, or metals selected from the group consisting of Na, Li, and Ca; and said reaction is optionally carried out in a mixture of acetic anhydride and/or acetic acid.

2. The method of claim 1, wherein the said alkyl, alkenyl comprise from 1~24 carbon atoms, said aryl comprises from 6~24 carbon atoms, said alkaryl, aralkyl comprise from 7~24 carbon atoms, and said cycloalkyl, heterocycloalkyl comprise from 3~24 carbon atoms.

3. The method of claim 1, wherein the said alkyl, alkenyl comprise from 1~18 carbon atoms, said aryl comprises from 6~18 carbon atoms, said alkaryl, aralkyl comprise from 7~18 carbon atoms, and said cycloalkyl, heterocycloalkyl comprise from 3~18 carbon atoms.

4. The method of claim 1, wherein $R_1$ and/or $R_2$ represent hydrogen.

5. The method of claim 1, wherein any two of $R_1$, $R_2$, $R_3$, $R_4$ and $R_5$ are together formed into a cycloalkyl, or heterocycloalkyl group.

6. The method of claim 5, wherein said cycloalkyl or heterocycloalkyl group is selected from 5, 6, 7 and 8 membered rings.

7. The method of claim 1, wherein $R_6$ and $R_7$ are together formed into a cycloalkyl, or heterocycloalkyl group.

8. The method of claim 7, wherein said cycloalkyl or heterocycloalkyl group is selected from 5, 6, 7 and 8 membered rings.

9. The method according to claim 1, wherein $R_1$, $R_2$ and $R_4$, represent hydrogen.

10. The method according to claim 1, wherein $R_3$ and $R_5$ represent methyl.

11. The method according to claim 1, wherein $R_1$, $R_2$, and $R_4$ represent hydrogen and $R_3$ and $R_5$ represent methyl.

12. The method according to claim 1, wherein $R_6$, and $R_7$ represent hydrogen.

13. The method according to claim 1, wherein said compound I or II is added in the molar ratio of (1~1.5):1 relative to said phosphorus acid or its derivates.

14. The method according to claim 13, wherein said compound I or II is added in the molar ratio of (1~1.2):1 relative to said phosphorus acid or its derivate.

15. The method according to claim 1, wherein the reaction time remains 4~24 hours.

16. The method according to claim 15, wherein the reaction time remains 4~8 hours.

17. The method according to claim 1, wherein the reaction temperature remains 0~100° C.

18. The method according to claim 17, wherein the reaction temperature remains 20~60° C.

* * * * *